(12) United States Patent
Doose et al.

(10) Patent No.: US 9,198,692 B1
(45) Date of Patent: Dec. 1, 2015

(54) SPINAL FIXATION ANCHOR

(75) Inventors: Justin Doose, San Diego, CA (US);
Scott Lish, Oceanside, CA (US);
Andrew Schafer, Ramona, CA (US);
Robert German, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 413 days.

(21) Appl. No.: 13/371,370

(22) Filed: Feb. 10, 2012

Related U.S. Application Data

(60) Provisional application No. 61/441,283, filed on Feb. 10, 2011, provisional application No. 61/444,698, filed on Feb. 18, 2011.

(51) Int. Cl.
*A61B 17/70* (2006.01)

(52) U.S. Cl.
CPC ......... *A61B 17/7032* (2013.01); *A61B 17/7085* (2013.01)

(58) Field of Classification Search
CPC .................................................. A61B 17/7085
USPC ................................ 606/246–279, 86 A, 306
See application file for complete search history.

(56) References Cited

U.S. PATENT DOCUMENTS

| 3,319,510 | A | * | 5/1967 | Rapata | F16B 19/1081 |
| | | | | | 24/297 |
| 4,109,691 | A | * | 8/1978 | Wilson | B25B 15/004 |
| | | | | | 411/3 |
| 4,569,259 | A | * | 2/1986 | Rubin | B25B 13/485 |
| | | | | | 411/402 |
| 5,002,542 | A | | 3/1991 | Frigg | |
| 5,047,029 | A | | 9/1991 | Aebi | |
| 5,196,013 | A | | 3/1993 | Harms et al. | |
| 5,209,752 | A | | 5/1993 | Ashman et al. | |
| 5,380,323 | A | | 1/1995 | Howland | |
| 5,443,467 | A | | 8/1995 | Biedermann | |
| 5,476,464 | A | | 12/1995 | Metz-Stavenhagen | |
| 5,501,684 | A | | 3/1996 | Hess | |
| 5,549,608 | A | | 8/1996 | Errico et al. | |
| 5,575,791 | A | | 11/1996 | Lin | |
| 5,584,831 | A | | 12/1996 | McKay | |
| 5,609,593 | A | | 3/1997 | Errico | |
| 5,681,319 | A | | 10/1997 | Biedermann | |
| 5,728,097 | A | | 3/1998 | Mathews | |
| 5,728,098 | A | | 3/1998 | Drewry | |
| 5,741,255 | A | | 4/1998 | Krag | |

(Continued)

FOREIGN PATENT DOCUMENTS

| AU | 723894 B2 | 2/1999 |
| CA | 2045502 | 5/1991 |

(Continued)

*Primary Examiner* — Eduardo C Robert
*Assistant Examiner* — Stuart S Bray
(74) *Attorney, Agent, or Firm* — Jonathan Spangler; Rory Schermerhorn

(57) ABSTRACT

This application describes surgical instruments and implants for building a posterior fixation construct across one or more segments of the spinal column. A fixation anchor is provided that includes a break off extension guide that extends from an anchor housing which captures a fixation rod. The extension guide has a guide channel that aligns with a rod channel in the housing to help direct the rod into the housing. The extension guide includes proximal breakable joints that allow the arms of the extension guide to be separated to facilitate rod insertion. Distal breakable joints are provided to allow the arms of the extension guide to be removed. Features and instruments for reducing the rod through the extension guide are also provided.

19 Claims, 9 Drawing Sheets

(56) References Cited

U.S. PATENT DOCUMENTS

| | | | |
|---|---|---|---|
| 5,752,957 A | 5/1998 | Ralph et al. | |
| 5,810,818 A | 9/1998 | Errico | |
| 5,879,350 A | 3/1999 | Sherman et al. | |
| 5,938,663 A | 8/1999 | Petreto | |
| 5,976,135 A | 11/1999 | Sherman et al. | |
| 6,063,090 A | 5/2000 | Schlapfer | |
| 6,074,391 A | 6/2000 | Metz-Stavenhagen | |
| 6,083,226 A | 7/2000 | Fiz | |
| 6,106,526 A | 8/2000 | Harms et al. | |
| 6,123,706 A | 9/2000 | Lange | |
| 6,132,432 A | 10/2000 | Richelsoph | |
| 6,179,838 B1 | 1/2001 | Fiz | |
| 6,183,473 B1 | 2/2001 | Ashman | |
| 6,187,005 B1 | 2/2001 | Brace | |
| 6,210,413 B1 | 4/2001 | Justis | |
| 6,231,575 B1 | 5/2001 | Krag | |
| 6,248,105 B1 | 6/2001 | Martin | |
| 6,280,442 B1 | 8/2001 | Barker et al. | |
| 6,402,749 B1 | 6/2002 | Ashman | |
| 6,454,773 B1 | 9/2002 | Sherman et al. | |
| 6,471,703 B1 | 10/2002 | Ashman | |
| 6,485,494 B1 | 11/2002 | Haider | |
| 6,520,962 B1 | 2/2003 | Taylor et al. | |
| 6,623,485 B2 | 9/2003 | Doubler et al. | |
| 6,626,906 B1 | 9/2003 | Young | |
| 6,648,887 B2 | 11/2003 | Ashman | |
| 6,660,004 B2 | 12/2003 | Barker et al. | |
| 6,685,705 B1 | 2/2004 | Taylor | |
| 6,802,844 B2 | 10/2004 | Ferree | |
| 6,835,196 B2 | 12/2004 | Biedermann et al. | |
| 6,872,209 B2 | 3/2005 | Morrison | |
| 6,964,666 B2 | 11/2005 | Jackson | |
| 7,022,122 B2 | 4/2006 | Amrein et al. | |
| 7,066,939 B2 | 6/2006 | Taylor | |
| 7,083,622 B2 | 8/2006 | Simonson | |
| 7,211,087 B2 | 5/2007 | Young | |
| 7,465,306 B2* | 12/2008 | Pond, Jr. | A61B 17/7079 606/104 |
| 7,892,238 B2 | 2/2011 | DiPoto | |
| 7,927,360 B2 | 4/2011 | Pond, Jr. | |
| 7,967,821 B2* | 6/2011 | Sicvol et al. | 606/86 A |
| 8,002,798 B2* | 8/2011 | Chin | A61B 17/7037 606/246 |
| 8,052,720 B2 | 11/2011 | Kuester | |
| 8,123,751 B2 | 2/2012 | Shluzas | |
| 8,262,662 B2* | 9/2012 | Beardsley et al. | 606/86 A |
| 8,308,728 B2* | 11/2012 | Iott et al. | 606/86 A |
| 8,372,084 B2* | 2/2013 | Pernsteiner | A61F 2/4425 606/86 A |
| 8,439,923 B2* | 5/2013 | Won | A61B 17/7037 606/264 |
| 8,496,661 B2 | 7/2013 | Moore | |
| 8,603,094 B2 | 12/2013 | Walker | |
| 8,623,061 B2 | 1/2014 | Quevedo | |
| 8,764,754 B2 | 7/2014 | Butler | |
| 8,784,424 B2 | 7/2014 | Tsuang | |
| 8,858,605 B1* | 10/2014 | Glatzer | A61B 17/7037 606/266 |
| 8,894,657 B2* | 11/2014 | Jackson | A61B 17/7008 606/104 |
| 8,956,361 B2* | 2/2015 | Davenport | A61B 17/7032 606/104 |
| 9,044,273 B2* | 6/2015 | Richelsoph | A61B 17/7001 |
| 2005/0131408 A1* | 6/2005 | Sicvol | A61B 17/7091 606/86 A |
| 2005/0192570 A1* | 9/2005 | Jackson | A61B 17/7032 606/914 |
| 2005/0277928 A1 | 12/2005 | Boschert | |
| 2006/0025771 A1* | 2/2006 | Jackson | A61B 17/7032 74/1 R |
| 2006/0036252 A1* | 2/2006 | Baynham | A61B 17/7035 606/308 |
| 2006/0095038 A1 | 5/2006 | Jackson | |
| 2006/0100622 A1 | 5/2006 | Jackson | |
| 2006/0111712 A1* | 5/2006 | Jackson | A61B 17/7037 606/914 |
| 2006/0111715 A1* | 5/2006 | Jackson | A61B 17/861 128/897 |
| 2006/0142761 A1 | 6/2006 | Landry et al. | |
| 2006/0149232 A1 | 7/2006 | Sasing | |
| 2006/0149240 A1 | 7/2006 | Jackson | |
| 2006/0179244 A1 | 8/2006 | Goodman et al. | |
| 2006/0200133 A1 | 9/2006 | Jackson | |
| 2006/0200136 A1 | 9/2006 | Jackson | |
| 2006/0241603 A1 | 10/2006 | Jackson | |
| 2006/0247630 A1* | 11/2006 | Iott | A61B 17/701 606/86 A |
| 2006/0247631 A1 | 11/2006 | Ahn et al. | |
| 2006/0271047 A1 | 11/2006 | Jackson | |
| 2006/0276789 A1 | 12/2006 | Jackson | |
| 2006/0276792 A1 | 12/2006 | Ensign et al. | |
| 2007/0016200 A1 | 1/2007 | Jackson | |
| 2007/0049933 A1 | 3/2007 | Ahn et al. | |
| 2007/0055240 A1 | 3/2007 | Matthis et al. | |
| 2007/0055241 A1 | 3/2007 | Matthis et al. | |
| 2007/0055244 A1 | 3/2007 | Jackson | |
| 2007/0073294 A1* | 3/2007 | Chin | A61B 17/7037 606/86 A |
| 2007/0088357 A1 | 4/2007 | Johnson et al. | |
| 2007/0093818 A1 | 4/2007 | Biedermann et al. | |
| 2007/0123862 A1 | 5/2007 | Warnick | |
| 2007/0123870 A1 | 5/2007 | Jeon et al. | |
| 2007/0167949 A1 | 7/2007 | Altarac et al. | |
| 2007/0173819 A1 | 7/2007 | Sandlin | |
| 2007/0233079 A1* | 10/2007 | Fallin | A61B 17/7085 606/86 A |
| 2007/0270810 A1 | 11/2007 | Sanders | |
| 2007/0299443 A1* | 12/2007 | DiPoto | A61B 17/02 606/86 A |
| 2008/0051780 A1 | 2/2008 | Vaidya et al. | |
| 2008/0119849 A1* | 5/2008 | Beardsley et al. | 606/61 |
| 2008/0119850 A1* | 5/2008 | Sicvol | A61B 17/7032 606/306 |
| 2008/0228228 A1* | 9/2008 | Hestad | A61B 17/025 606/246 |
| 2008/0275456 A1* | 11/2008 | Vonwiller | A61B 17/7032 606/246 |
| 2008/0300638 A1* | 12/2008 | Beardsley et al. | 606/306 |
| 2008/0312704 A1* | 12/2008 | Hestad | A61B 17/7085 606/86 A |
| 2009/0005814 A1* | 1/2009 | Miller | A61B 17/7037 606/246 |
| 2009/0216281 A1* | 8/2009 | Vonwiller et al. | 606/279 |
| 2009/0240292 A1* | 9/2009 | Butler | A61B 17/7085 606/86 A |
| 2010/0331901 A1* | 12/2010 | Iott et al. | 606/86 A |
| 2011/0040335 A1 | 2/2011 | Stihl | |
| 2011/0087293 A1* | 4/2011 | Ferreira | A61B 17/708 606/265 |
| 2011/0202095 A1* | 8/2011 | Semler | A61B 17/708 606/308 |
| 2011/0238117 A1* | 9/2011 | Geist | A61B 17/7083 606/263 |
| 2012/0109208 A1 | 5/2012 | Justice | |
| 2012/0303055 A1* | 11/2012 | Marik | A61B 17/708 606/205 |
| 2013/0012999 A1* | 1/2013 | Petit | A61B 17/7076 606/279 |
| 2013/0103096 A1* | 4/2013 | Miller | A61B 17/7032 606/305 |
| 2014/0100613 A1* | 4/2014 | Iott | A61B 17/7083 606/279 |

FOREIGN PATENT DOCUMENTS

| | | |
|---|---|---|
| WO | 98/32386 | 7/1998 |
| WO | 98/52482 | 11/1998 |
| WO | 2006/029373 | 3/2006 |
| WO | 2008/013892 | 1/2008 |

* cited by examiner

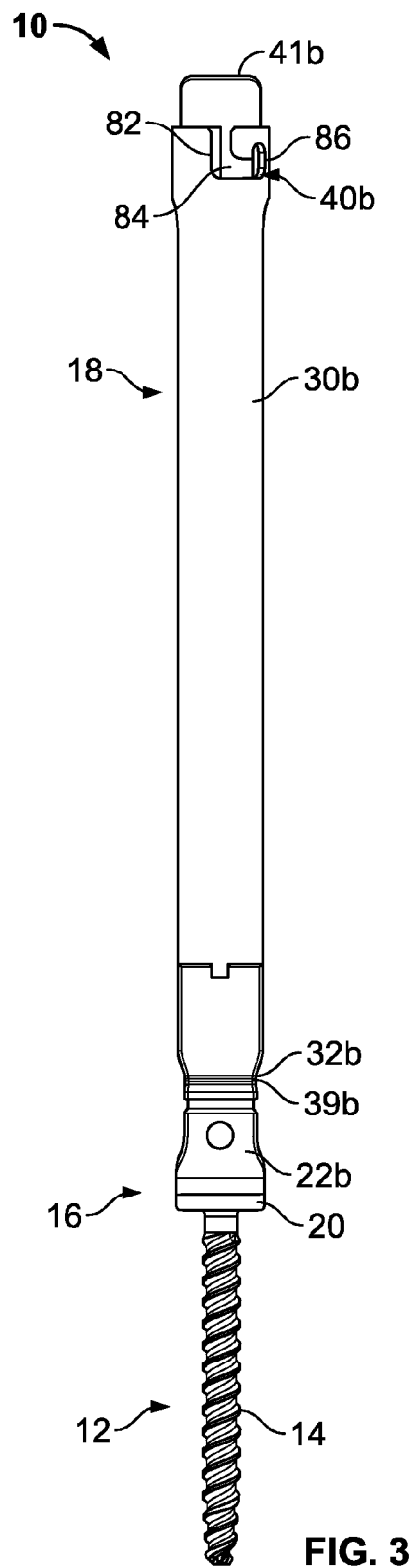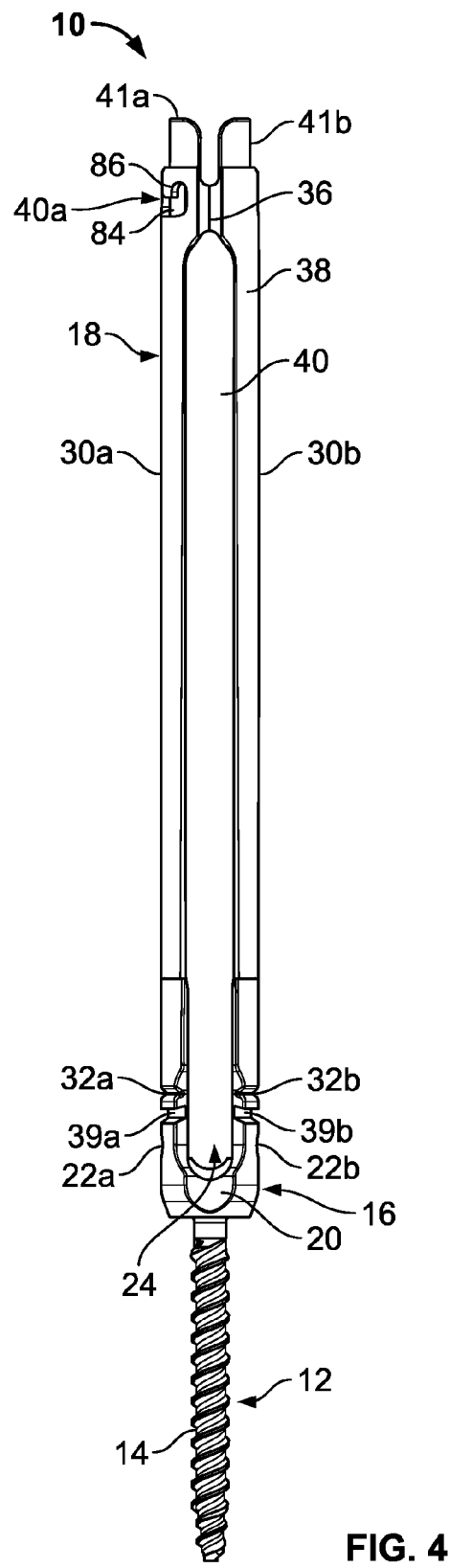
FIG. 3
FIG. 4

SPINAL FIXATION ANCHOR

CROSS-REFERENCES TO RELATED APPLICATIONS

This application is a non-provisional patent application claiming the benefit of priority from U.S. Provisional Patent Application Ser. No. 61/441,283, filed on Feb. 10, 2011, and U.S. Provisional Patent Application Ser. No. 61/444,698, filed on Feb. 18, 2011 the entire contents of which are each hereby expressly incorporated by reference into this disclosure as if set forth in its entirety herein.

FIELD

This application describes surgical instruments and implants for building a posterior fixation construct across one or more segments of the spinal column.

BACKGROUND

Spinal fixation constructs are utilized to provide stability to the spine. Most often the fixation construct is used as an adjunct to fusion surgery during which adjacent vertebrae are prepared to facilitate bone growth between them, thereby eliminating motion between the vertebrae. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved. Fixation constructs of various forms are well known in the art. Most commonly, the fixation construct is a plate anchored to the anterior column with multiple bone anchors or a posterior fixation construct including multiple anchors and a connecting rod anchored to the posterior elements of the spine. For a posterior fixation construct the anchors (typically pedicle screws) are anchored into the pedicles of each vertebra of the target motion segment. The anchors are then connected by a fixation rod that is locked to each anchor, thus eliminating motion between the adjacent vertebrae of the motion segment. The posterior fixation construct may be applied unilaterally or bilaterally. Additionally the posterior fixation construct may be applied across multiple levels or motion segments.

The fixation anchors utilized in posterior fixation constructs generally include an anchor portion and a rod housing. The rod housing includes a pair of upstanding arms separated by a rod channel in which the fixation rod is captured and locked. When constructing the posterior fixation construct the surgeon must align and seat the rod in the rod channel. This can be a challenge, particularly when one or more of the vertebrae to be connected is out of alignment leaving the associated anchor offset vertically and/or horizontally from the remaining anchor(s) of the construct. Constructing the posterior fixation construct under minimally invasive access conditions (e.g. minimizing overall incision length and muscle stripping as compared to traditional open procedures) also increases the difficulty of aligning the rod with the rod channel of the anchor.

The instruments, tools, and techniques described herein are directed towards reducing these challenges and others associated with posterior spinal fixation.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 3-4 are side and front views, respectively, of the spinal fixation anchor of FIG. 1;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation anchor disclosed herein boasts a variety of inventive features and components that warrant patent protection, both individually and in combination.

The present application describes a spinal fixation anchor 10 that may be utilized to form a fixation construct across one or more spinal levels of a patient. The spinal fixation anchor may be especially useful in forming fixation constructs across multiple spinal levels and/or spines with alignment deformities requiring correction. The spinal fixation anchor includes integral reduction features that may be utilized to seat a fixation rod in the anchor while realigning the position of the associated vertebra relative to other vertebra associated with the fixation construct. Additionally, separate reduction tools that cooperate with the spinal fixation anchor may be utilized to help seat the rod and realign the associated spinal segment. The spinal fixation anchor may also aid in installation of the fixation construct under minimally invasive conditions. That is, the overall length of skin incisions required to install the fixation construct may be minimized compared to traditionally open pedicle screw procedures. For example, the spinal fixation anchor includes an extension guide that extends distally out of the patient when the anchor is engaged to the spine. An elongated rod channel through the extension guide helps direct the rod into the proper position without requiring the extended incisions needed to fully expose the spinal segments to be fixated.

Figures 1, 2:
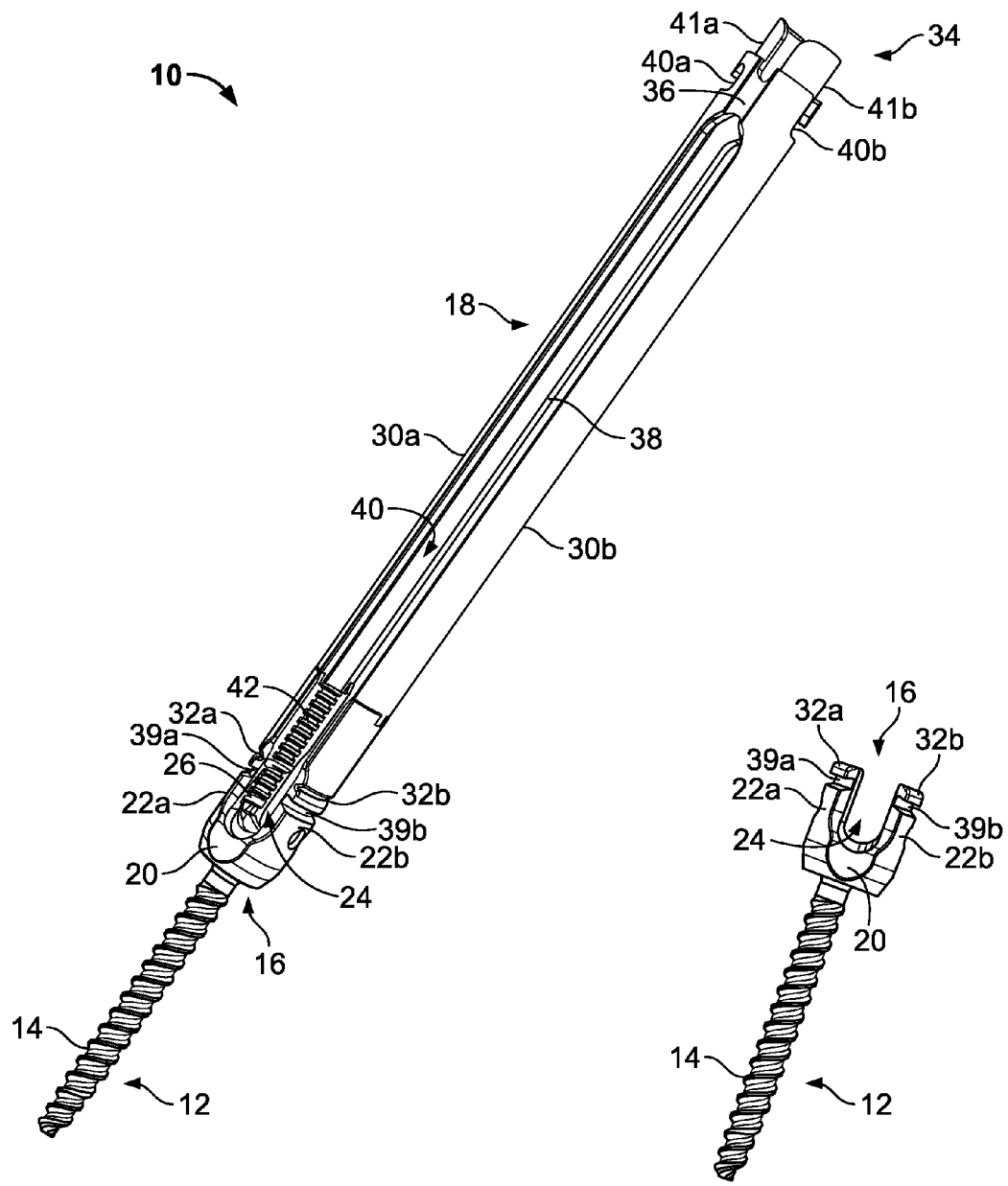
FIG. 1 is a perspective view of the spinal fixation anchor according to an example embodiment.
FIG. 2 is a perspective view of an implantable portion of the fixation anchor of FIG. 1 after removal of an extension guide.

Turning to FIGS. 1-2, there is depicted a spinal fixation anchor 10, according to an example embodiment. The fixation anchor 10 includes a bone anchor 12 (e.g. shank with thread feature 14) suitable for stable fixation to vertebral bone and a housing 16 for capturing and locking a fixation rod 50. Attached to the housing 16 is a break-off extension guide 18. The extension guide 18 helps align the rod 50 with the housing 16 and also helps reduce the rod into the housing when necessary. After the rod 50 is locked within housing 16 the extension guide 18 can be removed from the housing so the incision can be closed over the fixation construct (FIG. 2 depicts the fixation anchor with the extension guide 18 completely removed).

The housing 16 has a base 20 that mates with the bone anchor 12 and a pair of upstanding arms 22a and 22b separated by a rod channel 24. The arms 22a and 22b are equipped with a locking cap guide and advancement feature 26, such as by way of example, a helically wound flange feature disposed on the interior face of each arm 22a and 22b. The locking cap guide and advancement feature mates with a complementary guide and advancement feature on a locking cap 51. The locking cap 51 engages the upstanding arms via the complementary guide and advancement features to press and lock the fixation rod 50 into the housing 16.

The housing 16 and anchor 12 may be mated with a polyaxial engagement such that the housing 16 can pivot relative to the anchor 12 in any direction. The engagement may also be such that the pivoting movement may be inhibited in one or more directions. By way of example, the housing 16 and anchor 12 may be mated with a uniplanar engagement such that the housing pivots relative to the anchor 12 in a single plane. The housing 16 and anchor 12 may also be fixed such that no movement is possible between the housing 16 and anchor 12.

Break-off extension guide 18 extends from the top of housing 16 and includes a pair of extension arms 30a and 30b. Extension arm 30a attaches to housing arm 22a via an integral but breakable distal joint 32a. Extension arm 30b attaches to the housing arm 22b via an integral but breakable distal joint 32b. The breakable distal joints 32a and 32b are formed by surface grooves which reduce the material thickness along the entire junction between the extension arms 30a, 30b and housing arms 22a, 22b, respectively, such that directing an appropriate force to the extension arm will snap the associated breakable joint. The extension arms 30a and 30b are dimensioned with a length such that the extension guide 18 extends from the housing 16 to a location outside of the patient when the fixation anchor 10 is in a fully implanted position and securely anchored to the vertebra. At a proximal end 34 of the extension guide 18 the extension arms 30a and 30b come together to form a pair of integral but breakable proximal joints 36. Opposed vertical surface grooves above the guide slots 38 reduce material thickness along each junction between the extension arms 30a and 30b to form the breakable proximal joints 36.

Figure 9:
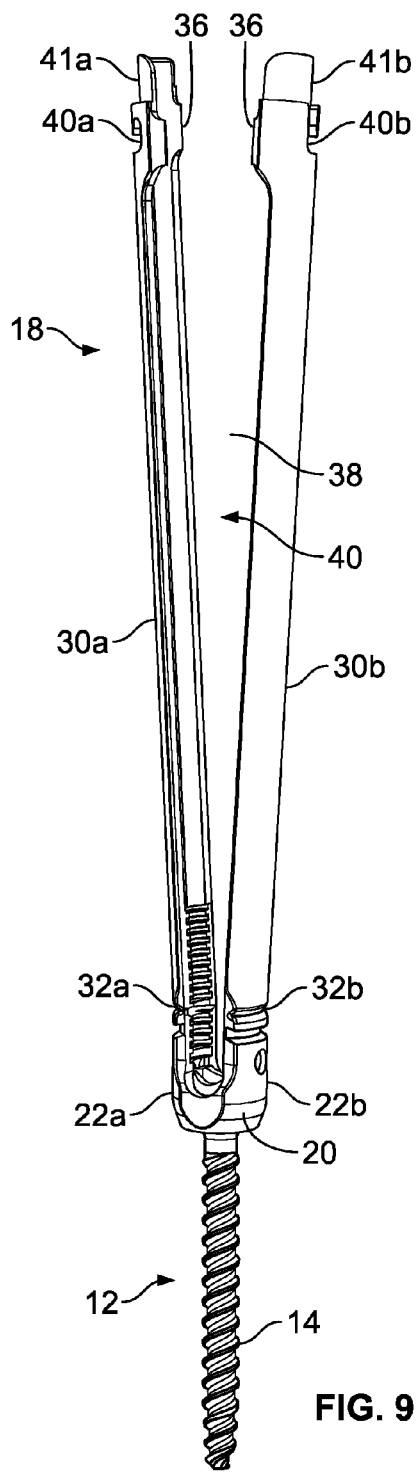
FIG. 9 is a front view of the fixation anchor of FIG. 1, after proximal joints are broken to allow the arms to separate.
Figure 10:
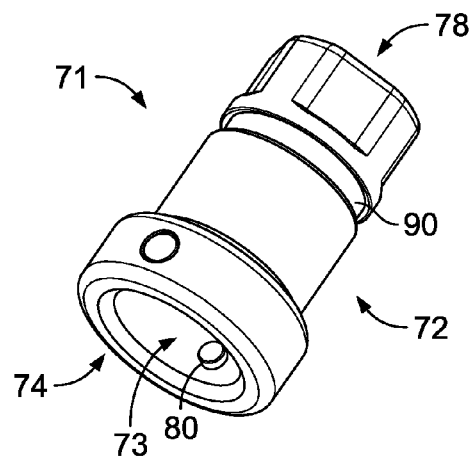
FIG. 10 is a perspective view of a guide cap for use with the fixation anchor of FIG. 1, according to one example embodiment.
Figure 11:
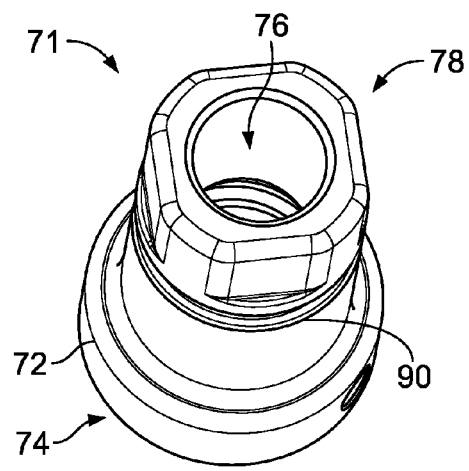
FIG. 11 is another perspective view of the guide cap of FIG. 10.
Figure 12:
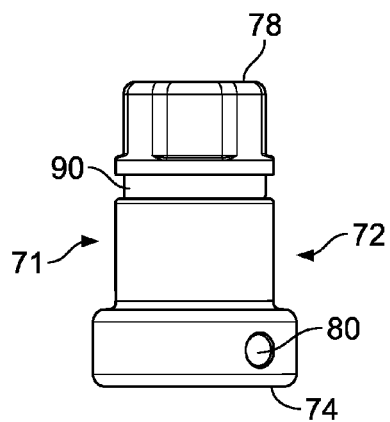
FIG. 12 is a side view of the guide cap of FIG. 10.
Figure 13:
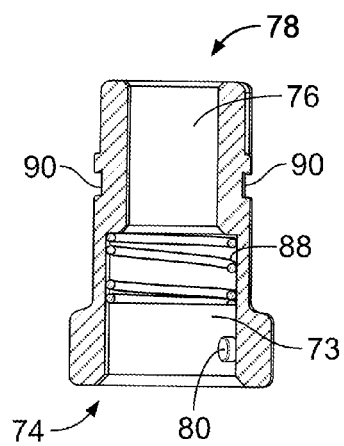
FIG. 13 is a cross section view of the guide cap as shown in FIG. 12.
Figure 14:
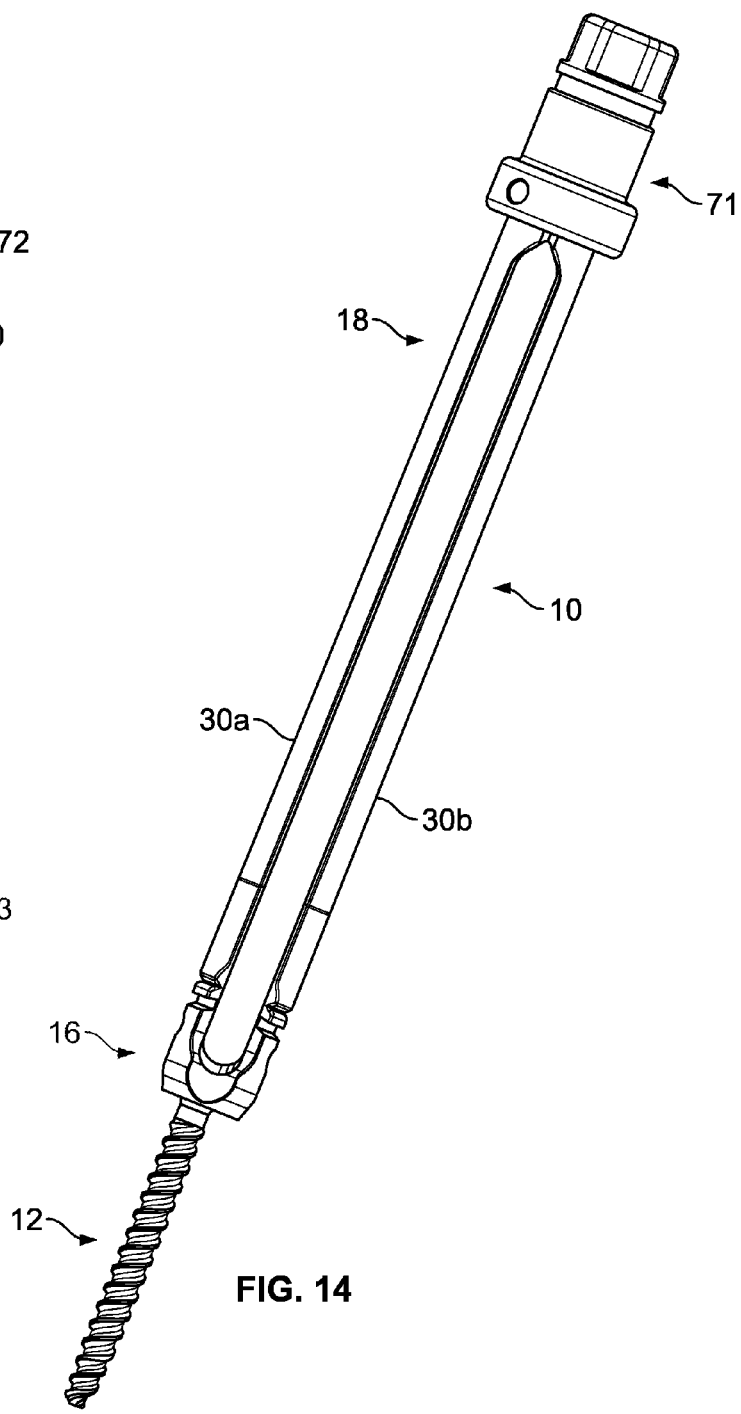
FIG. 14 is a perspective view of the guide cap of FIG. 10 coupled to the fixation anchor of FIG. 1.

Opposed guide slots 38 formed between arms 30a and 30b align with the rod channel 24 of the anchor housing 16 to define an enclosed guide channel 40 which is dimensioned to allow passage of a fixation rod 50. Utilizing the guide channel 40 to align the rod 50 with the housing rod channel 24 reduces the need for fiddlesome manipulation of the housing and/or rod down near the target site, as well as the associated need to fully visualize the housing 16 during rod insertion. Thus, the overall size of the incision required to implant a fixation construct using fixation anchors 10 is significantly reduced compared to open procedures. Though not necessary, after the anchor 10 is implanted, and to help facilitate rod insertion, the proximal joints 36 may be broken, thereby severing the proximal connection of the extension arms 30a and 30b and allowing the arms 30a and 30b to flex apart (FIG. 9). After breaking the proximal joints 36, a guide cap 71 (described below) may be used to reassociate the extension arms 30a and 30b if desired. Recess 40a on the proximal end of extension arm 30a and recess 40b on the proximal end of extension arm 30b facilitate the releasable coupling of the guide cap 71 to the proximal end 34 of the extension guide 18.

Figure 5:
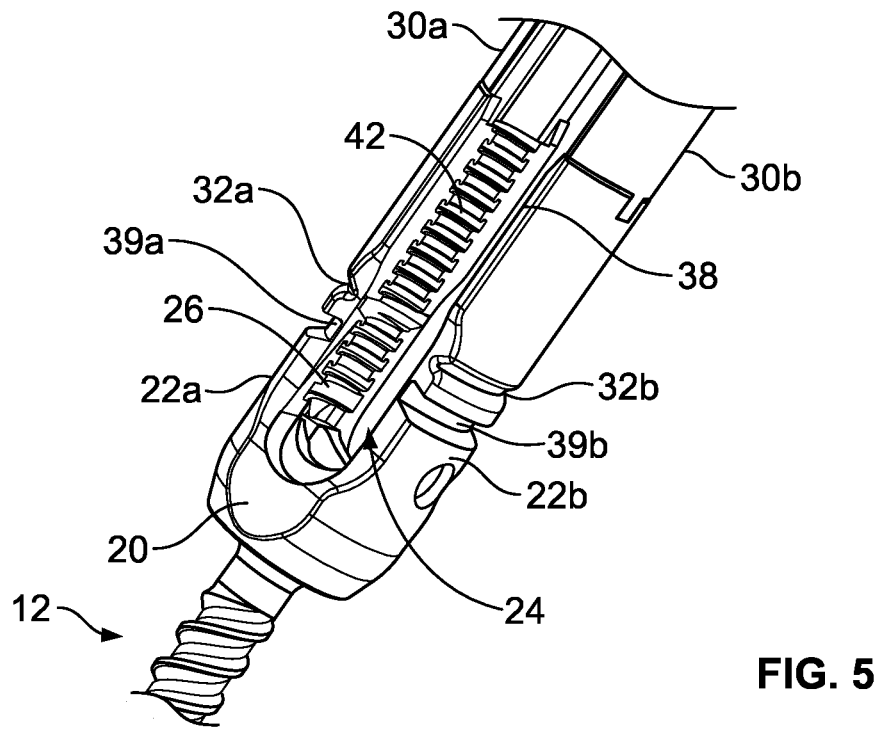
FIG. 5 is an enlarged perspective view of the junction between the implantable portion and extension guide of the fixation anchor of FIG. 1.
Figure 6:
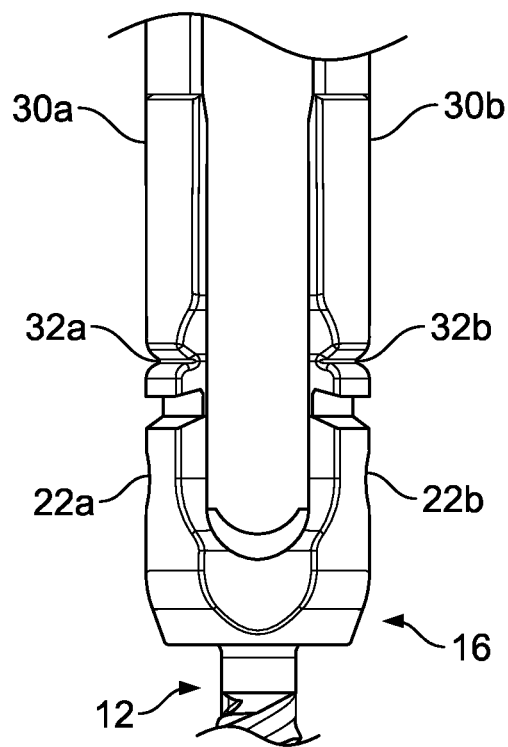
FIG. 6 is an enlarged front view of the junction region between the implantable portion and extension guide of the fixation anchor of FIG. 1.

As best pictured in FIG. 5, the fixation anchor 10 includes an integral reduction feature which provides for effective, single step reduction and locking when the spinal alignment necessitates the rod be reduced into the housing 16. The distal ends of extension arms 30a and 30b are appointed with a locking cap guide and advancement feature 42 situated adjacent to the breakable distal joints 32a and 32b. The guide and advancement feature 42 matches the guide and advancement feature 26 on the interior face of arms 22a and 22b. Further, the guide and advancement feature 42 is timed with the guide and advancement feature 26 such that the locking cap 51 advances seamlessly from the extension guide 18 to the housing 16. This configuration provides a mechanical advantage when advancing the locking cap 51 along the guide and advancement features 42 and 26, allowing the locking cap 51 to drive the rod into the housing 16 until it is fully seated and locked in position.

At some point during the surgical procedure after the fixation anchor(s) are anchored securely to their respective vertebra, the breakable distal joints 32a, 32b and the breakable proximal joints 36 must be broken in order to remove the break-off extension guide 18. The distal joints 32a and 32b are preferably broken only after the rod 50 is seated in the housing 16 and the locking cap 51 is fully engaged. In the event the extension guide 18 is removed prematurely and a guide structure is still desireable (e.g. for rod insertion, locking cap engagement, and/or reduction purposes), an attachment groove 39a is formed in the housing arm 22a and an attachment groove 39b is formed in housing arm 22b. A slip on guide structure (not shown) may be advanced and releasably coupled to the housing via the attachment grooves 39a, 39b. The proximal breaking joints 36 are preferably broken first before attempting break the distal joints 32a, 32b. This may be done just prior to breaking the distal joints to remove the extension guide after the rod 50 is seated and the locking cap 51 fully engaged in the housing 16. Alternatively, the surgeon may want to sever the connection between the extension arms 30a, 30b at an earlier point during the procedure. By way of example, the proximal joints 36 may be severed prior to rod insertion in order to facilitate easier rod insertion.

Figure 7:
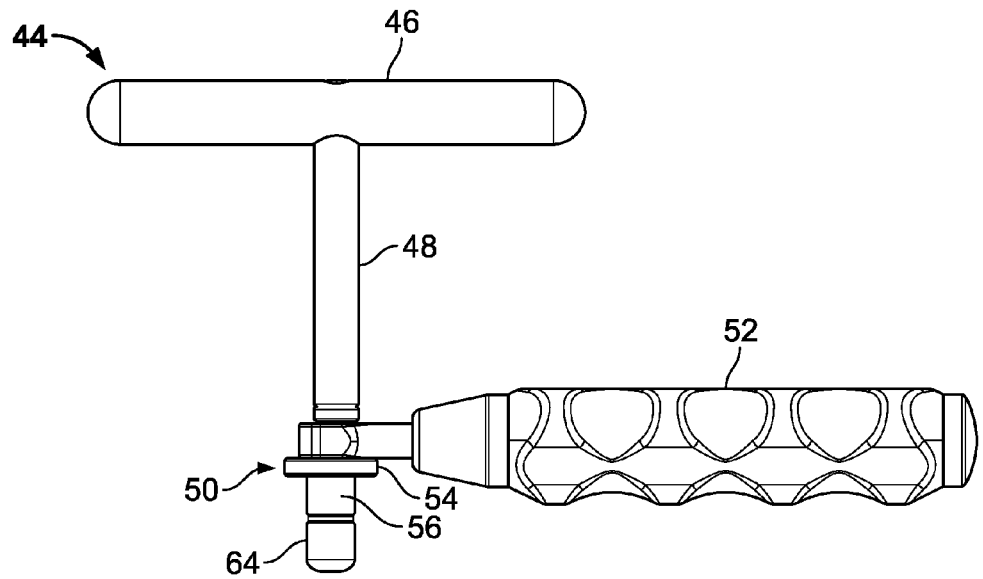
FIG. 7 is a side view of a breaking tool, according to an example embodiment.
Figure 8:
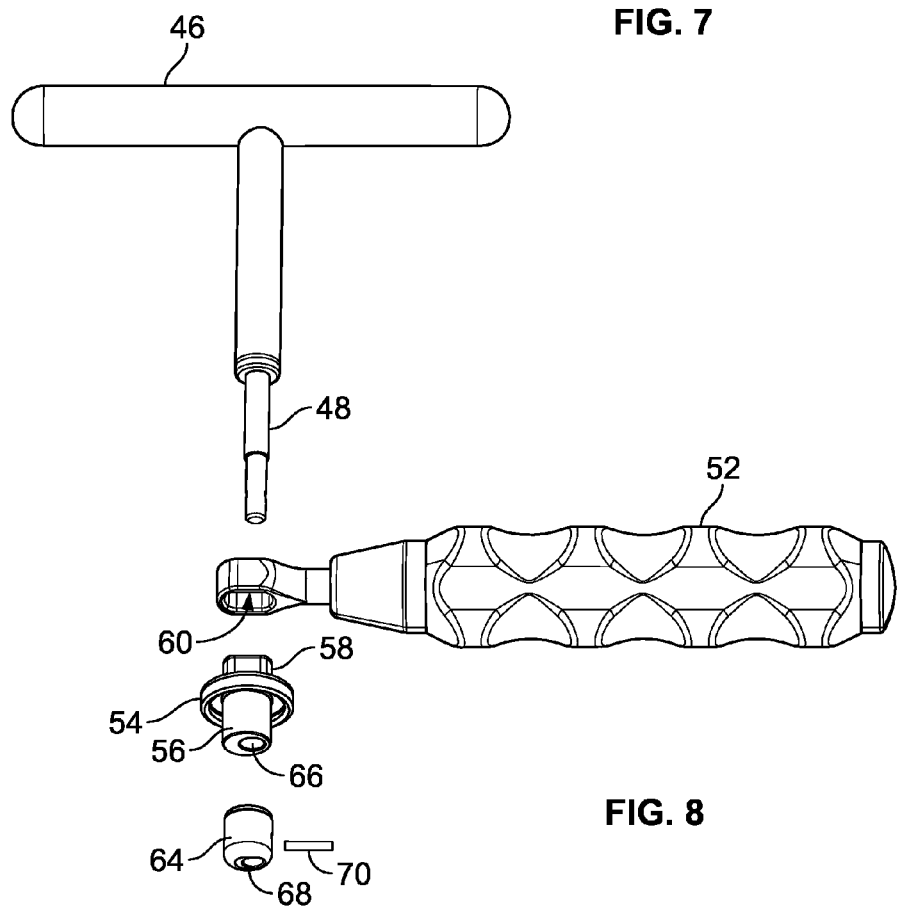
FIG. 8 is an exploded perspective view of the breaking tool of FIG. 7.

With reference to FIGS. 7-8, an example embodiment of a breaking tool 44 that may be utilized to break the proximal joints 36 is illustrated. The breaking tool 44 is designed to apply an outwardly directed force to the proximal joints 36 from inside the extension guide 18. The breaking tool 44 is a cam driver and includes a handle 46, rotating drive shaft 48, a cam 64 coupled to a distal end of the drive shaft 48, a hub 50, and a counter torque handle 52. The hub 50 has central cap 54 from which a cylinder 56 extends distally and a faceted block 58 extends proximally. The cylinder 56 has an exterior diameter that is slightly smaller than an interior diameter of the extension guide 18 such that the cylinder 56 can be passed into the extension guide 18. The central cap 54 has a diameter that is larger than the extension guide 18 such that the cap 54 controls the depth of insertion into the extension guide 18, ensuring force is applied in the right locations (i.e. on or near the proximal joints 36). The faceted block 58 mates with a complementary receptacle 60 attached to the counter torque handle 52 to prevent rotation of the hub 50 when the drive shaft 48 is operated.

A tunnel 66 dimensioned to receive a portion of the drive shaft 48 therethrough extends through the hub 50 along a line offset from a center axis of the cylinder 56. The cam 64 has a diameter that matches approximately the diameter of the cylinder 56 and a tunnel 68 for receiving the drive shaft 48 that is offset from the center axis of the cam. The cam 64 is fixed to the drive shaft 48 via pin 70 such that rotation of the drive shaft 48 causes the cam 64 to rotate relative to the cylinder 56. When the cam 64 and cylinder 56 are aligned they can slide together into the extension guide 18. As the cam 64 is rotated relative to the cylinder 56 the combined diameter of the two components expands, directing an outward force onto the extension arms 30a, 30b which causes the breakable proximal joints 36 to break, allowing the extension arms 30a, 30b to separate, as shown in FIG. 9. With the proximal joints 36 severed, the distal breakable joints 32a and 32b can be broken simply by bending the associated extension arm until the joint snaps. This can be done using a common grasping tool, such as forceps for example, or grasping the extensions arms directly with the hand.

While breaking the proximal joints 36 may have desirable consequences prior to and during rod insertion, it may also be desirable to have the rigidity associated with the unbroken guide extension 18 at later points during the surgery. To this end, a guide cap 71 is provided which may be used to hold the arm extensions 30a and 30b together and restore the rigidity of the unbroken guide extension 18. The guide cap 71 has a body 72 with a first internal cavity 73 opening out to a distal end 74 and a second internal cavity 76 opening out to a proximal end 78. The first internal cavity 73 has an internal diameter that is just larger than the external diameter of the extension guide 18 such that the proximal end of the extension guide may be received in the first internal cavity 73. The second internal cavity 76 has a diameter smaller than the first internal cavity 73, to provide a shelf for spring 88, approximating the internal diameter of the extension guide 18 and large enough to pass a locking cap 51 therethrough. A pair of opposed projections 80 extend into the first internal cavity 73 and engage with the recesses 40a and 40b on the extension arms 30a and 30b to releasably couple the guide cap 71 to the extension guide 18. The recesses 40a and 40b each include an open vertical slot 82 connected to one end of a horizontal slot 84, and a closed vertical slot 86 connected to the opposite end of the horizontal slot. To attach the guide cap 71, the projections 80 are aligned with the open vertical slots 82 and pressure is applied to the guide cap 71 such that the cap advances onto the extension guide 18. When the projections 80 reach the bottom of the open vertical slot 82 the cap is rotated until the projections 80 reach the end of the horizontal slot 84. Pressure is then released from the guide cap 71 and a spring 88 working against proximal tabs 41a, 41b of the extension arms draws the projections 80 into the closed vertical slots 86, thereby securing the guide cap 71 to the extension guide 18.

Figure 15:
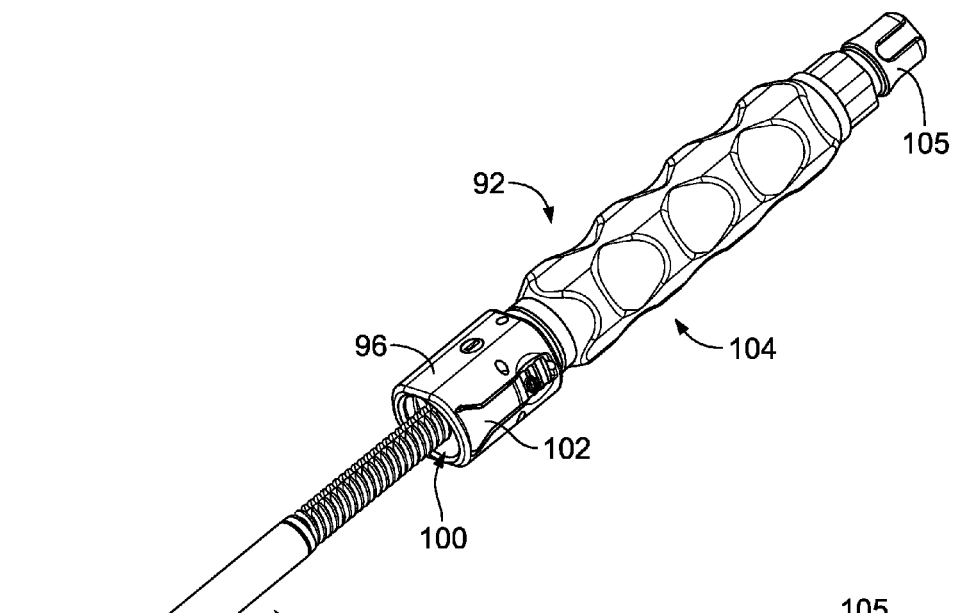
FIG. 15 is a perspective view of an independent reduction tool that may be used with the guide cap and fixation anchor of FIG. 15.

The reduction capabilities of the extension guide 18 are enhanced with the use of the guide cap 71. By way of example, the integral reduction features described above are less effective when the extension arms 40a and 40b are flexible and allowed to splay. The guide cap 71 negates this challenge such that the surgeon is not required to choose between easier rod insertion or better reduction. In addition, the body 72 of the guide cap 71 is adapted to releasably mate with independent reduction instruments should such an instrument be desired over the integral reduction features of the extension guide 18. One example of such an independent reduction instrument is depicted in FIG. 15.

Figure 16:
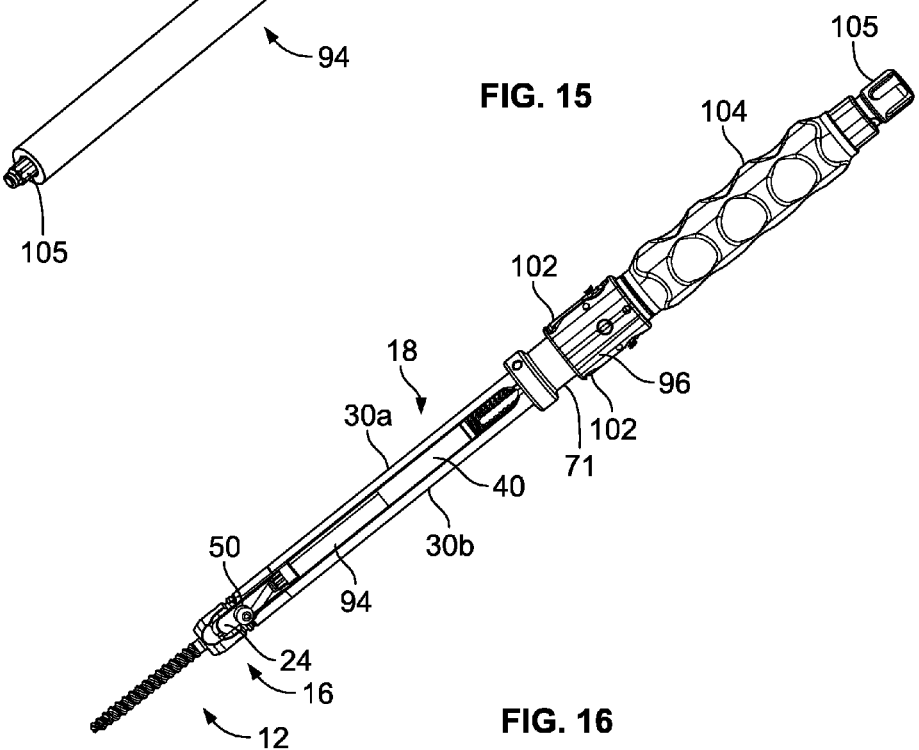
FIG. 16 is a front view of the independent reduction tool coupled to the guide cap and fixation anchor of FIG. 16.
Figure 17:
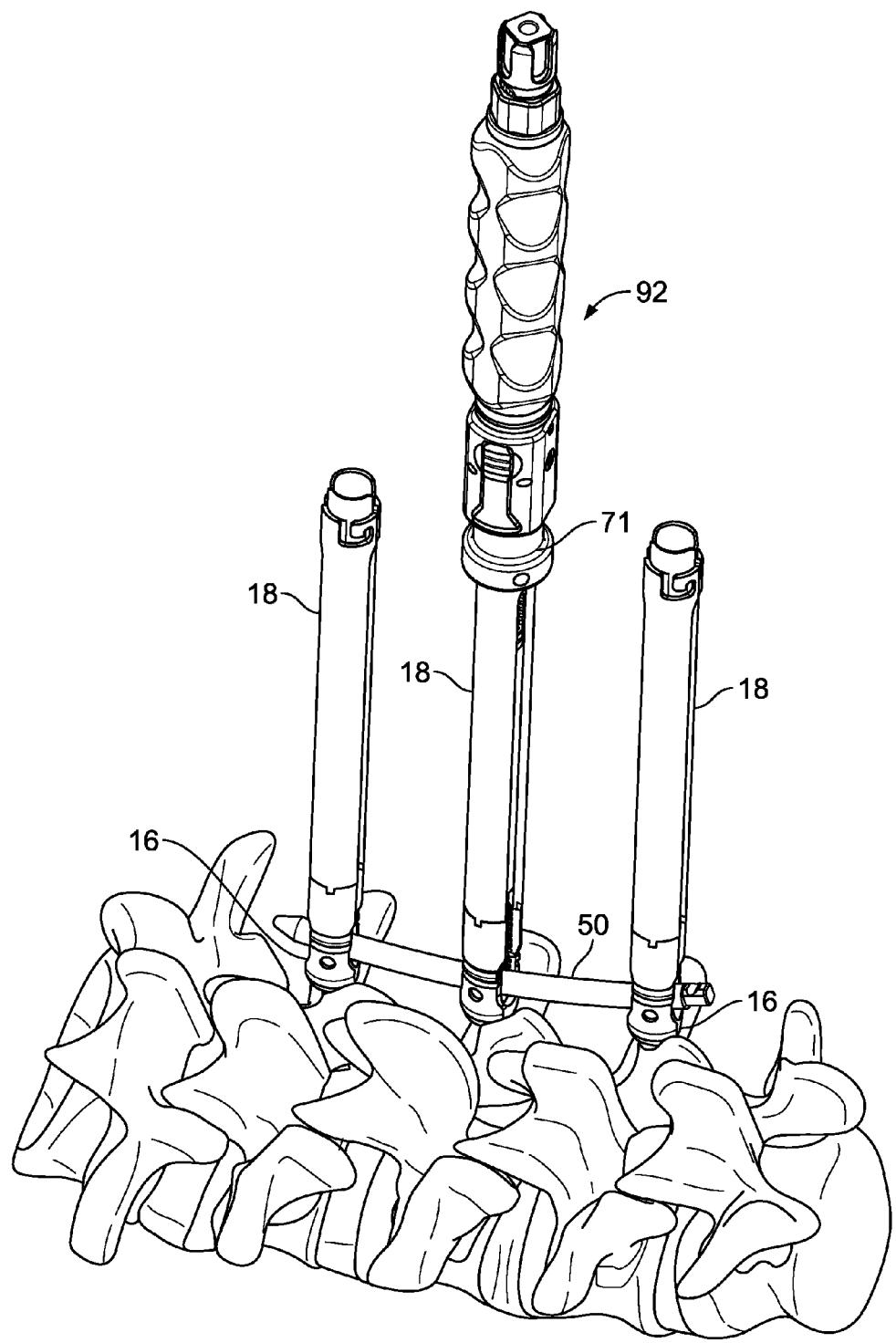
FIG. 17 is a perspective view of a lumbar spine illustrating the use of spinal fixation anchors of FIG. 1 with the guide cap of FIG. 10 and independent reduction instrument of FIG. 15 to implant a two level fixation construct, according to one example.

The reduction instrument 92 includes a connector 96 that releasably couples the reduction instrument to the extension guide (via guide cap 71). The connector 96 has a receptacle 100 into which the proximal end 78 of the guide cap 71 is received. The proximal end 78 is keyed to the receptacle 100 so as to prevent rotation of the guide cap 71 and attached extension guide 18 relative to reduction instrument 92. Spring clips 102 on the connector engage a groove 90 situated below the proximal end 78 to prevent translation of the guide cap 71 and attached extension guide 18 relative to the reduction instrument 92. The spring clips 102 have a tapered distal edge that extends into the receptacle 100. The tapered edge allows the proximal end 78 to push past the spring clips 102 until the tapered edge returns to rest in groove 90. To release the connection between the reduction instrument 92 and the guide cap 71 the proximal ends of the spring clips can be depressed and the connector 96 lifted off the proximal end 78. In use, the reduction shaft 94 is inserted through the guide cap 71 into extension guide 18 until the proximal end 78 of the guide cap 71 is locked into the receptacle 100, as illustrated in FIGS. 16-17. A reduction handle 104 may then be operated to translate the reduction shaft 94 distally relative to the extension guide 18 to drive the rod 50 through the guide channel 40 until the rod is fully seated in the housing 16. A locking cap driver 105 may then be operated to advance the locking cap 51 into the housing 16 and lock the rod 50 in place.

Having described the various features of the fixation anchor 10 and associated instruments, an example method for the minimally invasive implantation of a spinal fixation construct will now be described. First, a spinal fixation anchor is anchored through the pedicle of each vertebra to be fixated (e.g. three vertebra as shown in FIG. 17). At least one of the spinal fixation anchors is the spinal fixation anchor 10. The remaining fixation anchors may also be the fixation anchor 10 (as in FIG. 17). Alternatively, the remaining fixation anchors may be anchors adapted for use with independent guide structures that releasably couple to the anchors, as are generally known in the art.

With the fixation anchors 10 in position, a rod 50 appropriately sized to span the distance between the end anchors is selected. At this point, the proximal joints 36 on one or more of the fixation anchors 10 may be broken if the surgeon chooses to do so. By way of example, the surgeon may choose to break the proximal joints 36 of the fixation anchor 10 at the opposite end of the construct from which rod insertion will be directed. During some insertion techniques the rod is inserted into the guide channel of the first fixation anchor 10 generally parallel to the extension guide while the insertion instrument is angled back towards the remainder of the extension guides 18. As the inserter is rocked towards the insertion end, the rod advances through each guide. Severing the proximal joints 36 on the extension guide 18 at the opposite end of the construct from rod insertion allows the inserter to advance between the extension arms 30a, 30b of the end anchor (instead of having to work the inserter around the outside of the guide extension 18). This simplifies passage of the rod by facilitating proper alignment of the rod during insertion. If the surgeon chooses to break the proximal joints 36, the cam 64 and cylinder 56 of the breaking tool 44 are aligned and inserted into the extension guide 18 until the cap 54 rests on the proximal end of the extension guide 18. The cam 64 is then rotated with one hand while the counter torque handle 52 is held in the other hand until the proximal joints 36 break apart. The rod 50 is then inserted through the guide channels 40.

If necessary, (for example, if the rod 50 does not fully seat within the anchor housing 16 as would be the case if or more of the vertebrae are not vertically aligned) one or more of the reduction methods described above may be employed to reduce the rod 50. If the rod 50 is seated low enough in the guide channel 40 that the guide and advancement features 42 are accessible above the rod then reduction may be accomplished by engaging a locking cap 51 with the guide and advancement features 42 and advancing the locking cap 51 until the rod 50 and locking cap 51 are fully seated in the housing 16. If this reduction is to be carried out on a fixation anchor 10 whose proximal joints 36 had been previously broken, the guide cap 71 should preferably be coupled to the extension guide 18 prior to reduction. Alternatively, if the rod 50 sits above the guide and advancement features 42 or the surgeon simply prefers to utilize an independent reduction tool, the guide cap 71 should be attached to the appropriate fixation anchor 10 whether or not the proximal joints 36 of that anchor have been broken. The independent reduction instrument 92 is then coupled to the extension guide 18 and operated to reduce the rod 50 into the housing 16 and a locking cap 51 is engaged to lock the rod 50 in place. The surgeon may choose to utilize both the integral reduction features for reduction at one fixation anchor 10 and the independent reduction instrument for reduction at another of the fixation anchors 10. Reduction (when necessary) and locking cap engagement is completed for each spinal fixation anchor in the construct.

Figure 18:
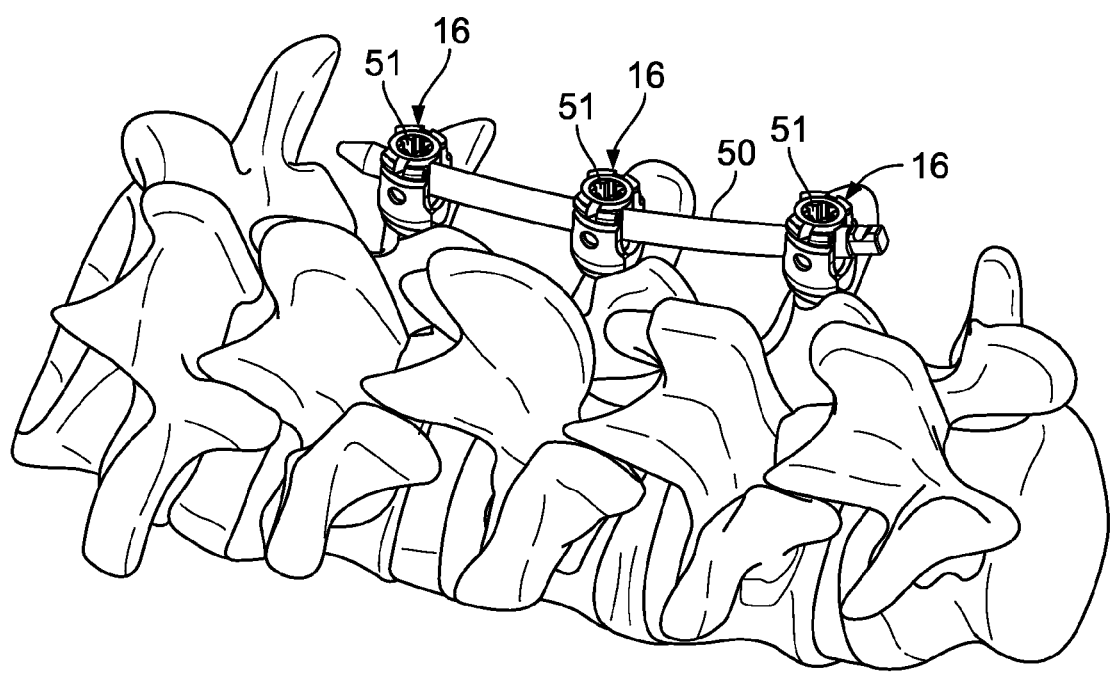
FIG. 18 is a perspective view of the lumbar spine of FIG. 17 after the locking caps have been deployed and extension guides have been removed to leave the final fixation construct.

With the rod 50 locked down along the entire construct the extension guide 18 should be removed. First, any guide caps 71 utilized during the procedure should be removed. Then the breaking tool 44 is used to break the proximal joints 36 of all extension guides 18 whose proximal joints 36 remain intact. Finally, the extension arms 30a and 30b of each spinal anchor 10 are removed by breaking the distal joints 40a and 40b, respectively. According to an alternative sequence, the extension guide 18 can be removed from each fixation anchor 10 in sequence as the rod 50 is locked to each anchor 10. Once the extension guides 18 are removed from each anchor 12, the final fixation construct is complete, as illustrated in FIG. 18, and the incision(s) can be closed.

While the inventive features described herein have been described in terms of a preferred embodiment for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

What is claimed is:

1. A spinal fixation anchor, comprising:
   an implantable portion including a bone anchor and a rod housing having a first arm separated from a second arm by a rod channel; and
   an extension guide integrally but breakably connected to the rod housing, the extension guide having an outer surface, an inner surface, and a material thickness defined between the outer surface and inner surface, the extension guide including a first extension arm having a distal end and a proximal end and a second extension arm having a distal end and a proximal end, the distal end of the first extension arm being connected to the first arm of the rod housing by a first breakable joint, the distal end of the second extension arm being connected to the second arm of the rod housing by a second breakable joint, the first breakable joint comprising a horizontal groove of reduced material thickness positioned between the first arm and the first extension arm, the second breakable joint comprising a horizontal groove of reduced material thickness positioned between the second arm and the second extension arm, the proximal end of the first extension arm being integrally but breakably connected to the proximal end of the second extension arm by third and fourth breakable joints, the first extension arm being separated from the second extension arm by a guide channel aligned with the rod channel and extending distally from the third and fourth breakable joints through the extension guide distal end, the guide channel having a first width dimensioned to permit passage of a rod therethrough, the third and fourth breakable joints each comprising a vertical groove of reduced material thickness positioned between the first and second extension arms, the vertical grooves of the third and fourth breakable joints each having a second width that is less than the first width of the guide channel.

2. The system of claim 1, further including a guide cap that is releasably coupleable to the proximal ends of the first and second extension arms.

3. The system of claim 2, wherein the guide cap is releasably coupleable to the proximal ends of the first and second extension arms after the third and fourth breakable joints are broken.

4. The system of claim 3, wherein the guide cap prevents the extension arms from flexing apart.

5. The system of claim 2, wherein the guide cap serves as a connection adapter between the extension guide and an independent instrument.

6. The system of claim 5, where the independent instrument is a reduction instrument.

7. The spinal fixation anchor of claim 1, wherein the rod housing includes a guide and advancement feature adapted to engage with a complementary guide and advancement feature on a locking cap.

8. The spinal fixation anchor of claim 7, wherein the distal end of the extension guide includes a guide and advancement feature that integrates with the guide and advancement feature of the rod housing.

9. A spinal fixation anchor system comprising;
   a fixation anchor, wherein the fixation anchor comprises:
      an implantable portion including a bone anchor and a rod housing having a first arm separated from a second arm by a rod channel; and
      an extension guide integrally but breakably connected to the rod housing, the extension guide having an outer surface, an inner surface, and a material thickness defined between the outer surface and inner surface, the extension guide including a first extension arm having a distal end and a proximal end and a second extension arm having a distal end and a proximal end, the distal end of the first extension arm being connected to the first arm of the rod housing by a first breakable joint, the distal end of the second extension arm being connected to the second arm of the rod housing by a second breakable joint, the proximal end of the first extension arm being integrally but breakably connected to the proximal end of the second extension arm by third and fourth breakable joints, the first extension arm being separated from the second extension arm by a guide channel aligned with the rod channel and extending distally from the third and fourth breakable joints through the extension guide distal end, the guide channel having a first width dimensioned to permit passage of a rod therethrough, the third and fourth breakable joints each comprising a vertical groove of reduced material thickness positioned between the first and second extension arms, the vertical grooves of the third and fourth breakable joints each having a second width that is less than the first width of the guide channel; and a locking cap that couples to the rod housing to lock a rod in position within the housing.

10. The system of claim 9, further including a guide cap that is releasably coupleable to the proximal ends of the first and second extension arms.

11. The system of claim 10, wherein the guide cap is releasably coupleable to the proximal ends of the first and second extension arms after the third and fourth breakable joints are broken.

12. The system of claim 11, wherein the guide cap prevents the extension arms from flexing apart.

13. The system of claim 10, wherein the guide cap serves as a connection adapter between the extension guide and an independent instrument.

14. The system of claim 13, where the independent instrument is a reduction instrument.

15. The system of claim 9, further including a breaking tool adapted to break the third and fourth breakable joints at the proximal end of the extension guide without breaking the first and second breakable joints at the distal end of the extension guide.

16. The system of claim 15, wherein the breaking tool includes a cam that is receivable within the extension guide.

17. A method for implanting a fixation construct across a motion segment of a spine, the method comprising:

establishing an operative corridor to the target motion segment;

anchoring a first fixation anchor to a first vertebra of the motion segment and anchoring a second fixation anchor to a second vertebra of the motion segment, wherein the first fixation anchor includes a first rod housing defining a first rod channel and a first extension guide integrally but breakably coupled to the first rod housing, the first extension guide having an outer surface, an inner surface, and a material thickness defined between the outer surface and inner surface, the first extension guide including a first extension arm having a distal end and a proximal end and a second extension arm having a distal end and a proximal end, the distal end of the first extension arm being connected to a first arm of the rod housing by a first breakable joint, the distal end of the second extension arm being connected to a second arm of the rod housing by a second breakable joint, the first breakable joint comprising a horizontal groove of reduced material thickness positioned between the first arm and the first extension arm, the second breakable joint comprising a horizontal groove of reduced material thickness positioned between the second arm and the second extension arm, the proximal end of the first extension arm being integrally but breakably connected to the proximal end of the second extension arm by third and fourth breakable joints, the first extension arm being separated from the second extension arm by a guide channel aligned with the rod channel and extending distally from the third and fourth breakable joints through the first extension guide distal end, the guide channel having a first width dimensioned to permit passage of a rod therethrough, the third and fourth breakable joints each comprising a vertical groove of reduced material thickness positioned between the first and second extension arms, the vertical grooves of the third and fourth breakable joints each having a second width that is less than the first width of the guide channel;

breaking the third and fourth breakable joints to sever the connection between the proximal ends of the first and second extension arms of the first extension guide such that the first and second extension arms can flex away from each other to facilitate rod insertion;

inserting a rod through the guide channel of the first anchor;

attaching a guide cap to the proximal end of the first extension guide to reconnect the first and second extension arms and prevent further flexing of the first and second extension arms away from each other;

reducing the rod into the first rod channel of the first rod housing;

locking the rod within the first rod housing with a locking cap;

locking the rod to the second fixation anchor; and breaking the first and second breakable joints to sever the connection between the first and second extension arms and the first and second arms of the first rod housing and removing the first and second extension arms from the operative corridor.

18. The method of claim 17, wherein the step of reducing the rod includes engaging the locking cap with a guide and advancement feature at the distal end of the extension guide.

19. The method of claim 17, wherein the step of reducing the rod includes coupling a reduction instrument to the guide cap and operating the reduction instrument.

* * * * *